US00PP19382P3

(12) United States Plant Patent
Goffreda et al.

(10) Patent No.: US PP19,382 P3
(45) Date of Patent: Oct. 28, 2008

(54) PEACH TREE NAMED 'NJ350'

(50) Latin Name: *Prunus persica*
Varietal Denomination: NJ350

(75) Inventors: Joseph C. Goffreda, Manalapan, NJ (US); Anna M. Voordeckers, East Windsor, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 238 days.

(21) Appl. No.: 11/371,384

(22) Filed: Mar. 9, 2006

(65) Prior Publication Data

US 2007/0214523 P1 Sep. 13, 2007

(51) Int. Cl.
*A01H 5/00* (2006.01)

(52) U.S. Cl. ..... Plt./197

(58) Field of Classification Search ..... Plt./197
See application file for complete search history.

*Primary Examiner*—Kent L. Bell
*Assistant Examiner*—Georgia Helmer
(74) *Attorney, Agent, or Firm*—James A. Lucas; Driggs, Hogg, Daugherty & Del Zoppo, Co., L.P.A.

(57) ABSTRACT

A new and distinct peach variety of *Prunus persica* named 'NJ350' is provided. This variety is distinguished from other peach varieties by its unique combination of nonshowy flowers, fruit that ripen early in the season, attractive fruit with an orange-red ground color, clingstone fruit with a juicy, melting texture and moderately acidic flavor, and good production of firm fruit with a low incidence of split pits for the season.

6 Drawing Sheets

Latin name of genus and species of the plant claimed: *Prunus persica* L.

BACKGROUND OF THE INVENTION

The present invention relates to a new and distinct variety of peach tree named 'NJ350'. Our new tree resulted from crossing 'Garnet Beauty' as the seed parent with 'Sentry' peach tree, as the pollen parent. The new variety differs from speed parent 'Garnet Beauty' (unpatented) in that the new variety has fruit with a rounded apex having an inconspicuous apex point, while the seed parent often has fruit with a prominent apex point. The new variety differs from pollen parent 'Sentry' (unpatented) in that the new variety has reniform leaf glands, while the parent has globose leaf glands. The new variety also ripens 7 to 10 days earlier than comparably cropped trees of either the seed or pollen parents. The resulting tree was selected when growing in a cultivated area as the 152$^{th}$ tree in the 81$^{th}$ row of Block D at the Rutgers Fruit Research and Extension Center in Cream Ridge, N.J.

BRIEF SUMMARY OF THE INVENTION

The 'NJ350' variety is distinguished from other peach varieties due to the following unique combination of characteristics:

Attractive round fruit with an inconspicuous apex point.

Fruit with an orange-red ground color.

Low incidence of split pits for season.

Good production of firm fruit.

The variety was asexually reproduced at the Rutgers Fruit Research and Extension Center in Cream Ridge, N.J. Asexual reproduction of this new variety by budding onto >Lovell=rootstock (unpatented) shows that the foregoing characteristics are so reproduced.

The following detailed description concerns the original tree, 'NJ350'. The original tree and asexual progeny have been observed growing in a cultivated area at the Rutgers Fruit Research and Extension Center in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The Royal Horticultural Society (R.H.S.) Colour Chart. Unless otherwise noted, the following photographs were taken of a typical tree that was four years of age

Figure 1:
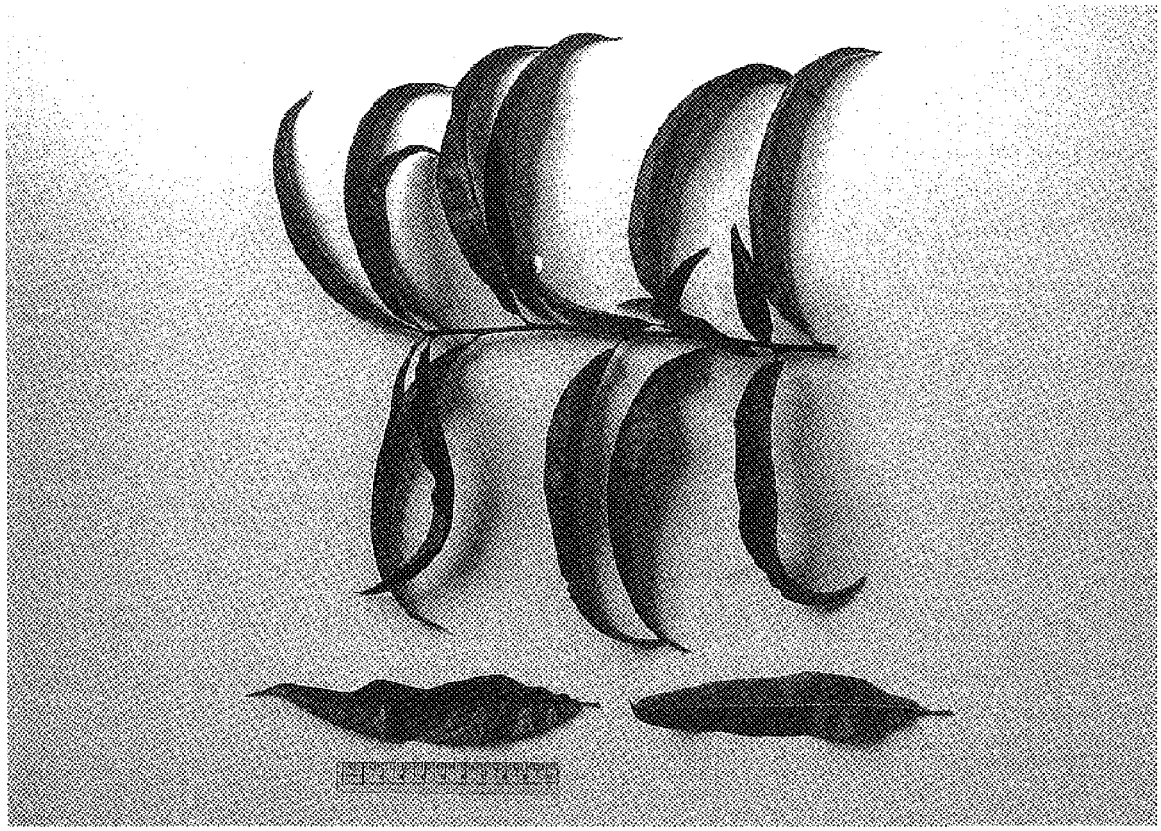
FIG. 1 is a color photograph taken on Aug. 29, 2005 of a characteristic twig of 'NJ350' in late summer bearing typical leaves of the mature foliage.
Figure 2:
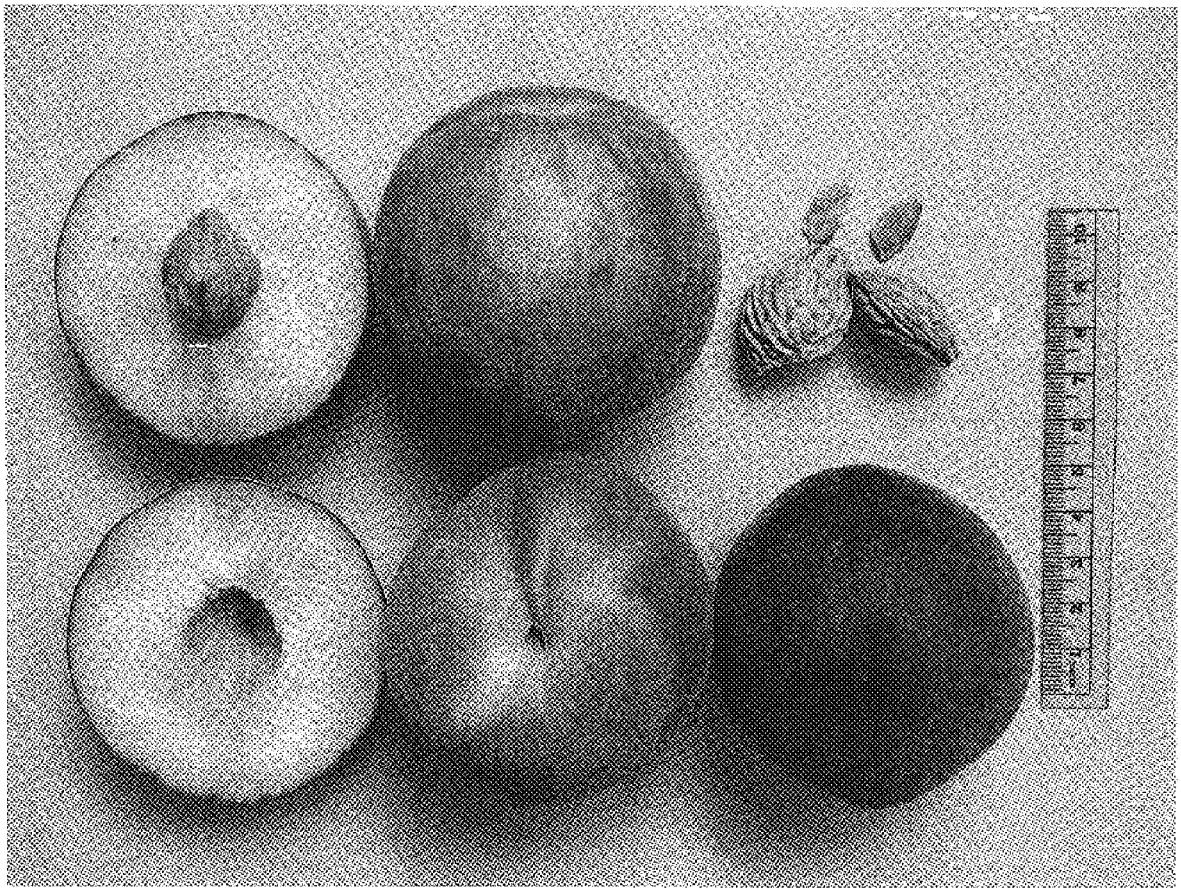
FIG. 2 is a color photograph of mature fruit of 'NJ350' and stones harvested from the Rutgers Fruit Research and Extension Center in Cream Ridge, N.J. on Jul. 25, 2005. Whole fruit are presented in three positions, a lateral view (upper center), a basal view (lower center) and an apical view (lower right). Transverse cross sections (upper left and lower left) are presented to show that the pericarp adheres to the pit when the fruit is mature. The stones (upper right) illustrate the medium, narrow, and fine lines of the dorsal ridge and the pit grooves on the surface of the stone.
Figure 3:
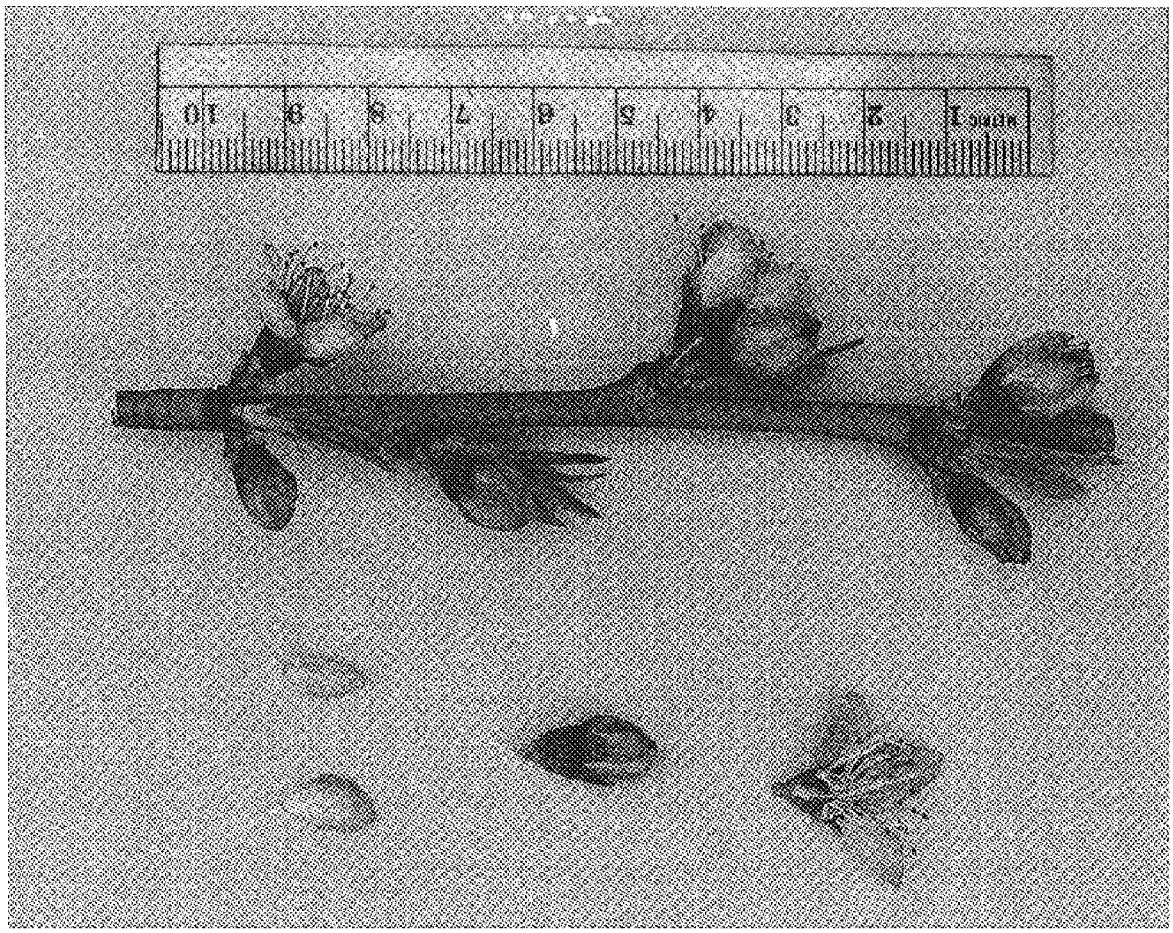
FIG. 3 is a color photograph of a characteristic twig that illustrates the typical flower buds and small, nonshowy flowers of 'NJ350' observed on a three year old tree at the Rutgers Fruit Research and Extension Center in Cream Ridge, N.J. on Apr. 21, 2004.
Figure 4:
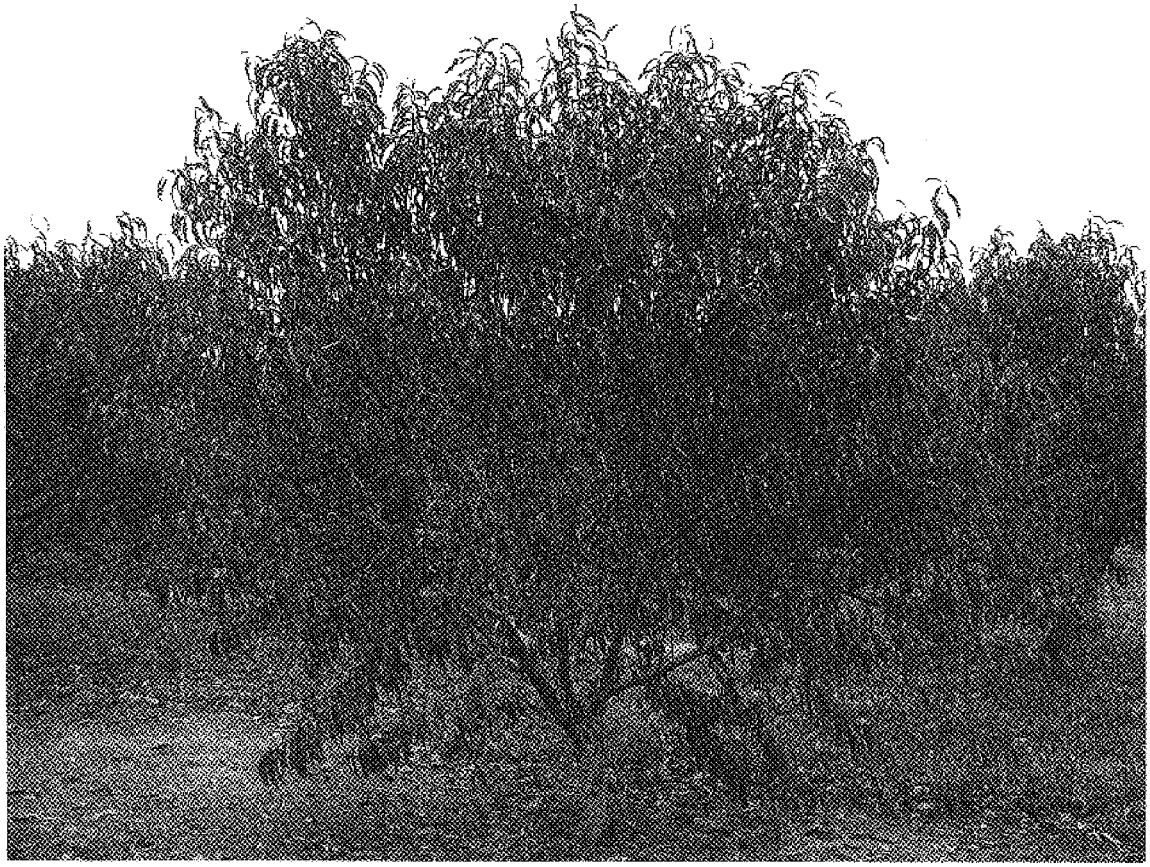
FIG. 4 is a color photograph of a tree of 'NJ350' in early fall that illustrates the spreading growth habit of a tree at the Rutgers Fruit Research and Extension Center in Cream Ridge, N.J. on Oct. 27, 2005.
Figure 5:
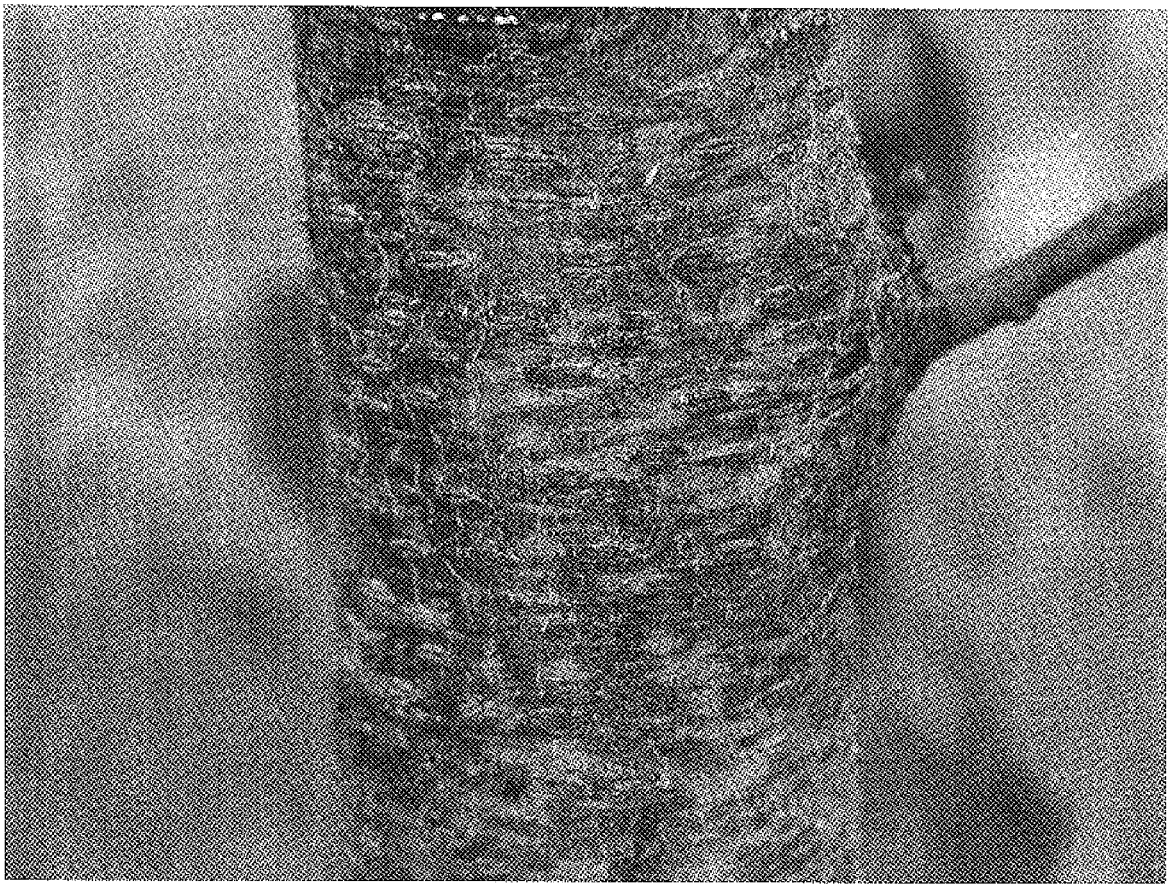
FIG. 5 is a color photograph taken on Oct. 27, 2005 of immature bark of 'NJ350' that illustrates color and the moderate density of elliptical lenticels on the immature bark.
Figure 6:
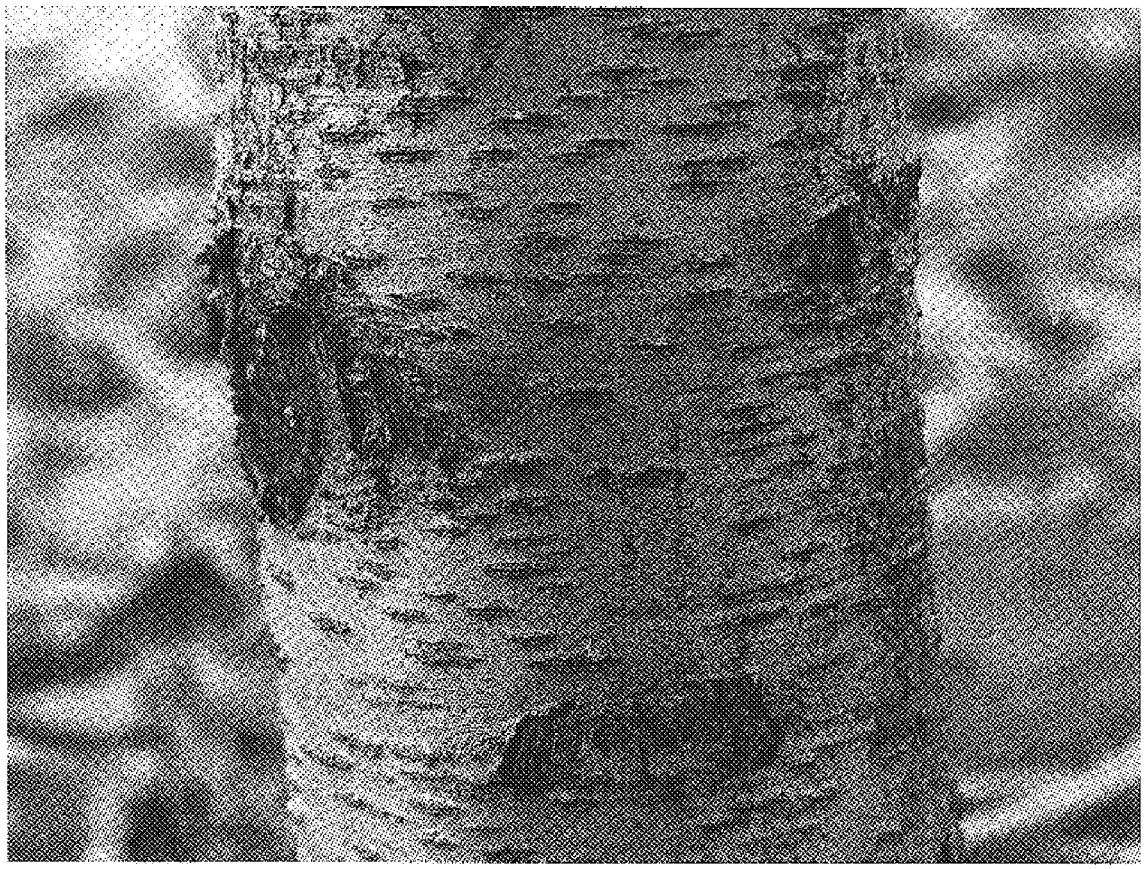
FIG. 6 is a color photograph taken on Oct. 27, 2005 of mature bark of 'NJ350' that illustrates the fairly smooth texture and prominent lenticels of the mature bark.

The colors and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJ350' variety is based on observations of an asexually reproduced tree. The observed tree was four years of age and growing on 'Lovell' seedling rootstock (unpatented) in Research Block E at the Rutgers Fruit Research and Extension Center in Cream Ridge, N.J.

Scientific name: *Prunus persica* L.
Parentage:

| | |
|---|---|
| Seed parent: | Garnet Beauty. |
| Pollen parent: | Sentry. |

Tree:

| | |
|---|---|
| Vigor: | Vigorous. |
| Plant hardiness zone: | Growth of plants has only been observed in zone 6b. |
| Dormant flower bud cold tolerance: | At least to −16° C. |
| Overall shape: | Spreading. |
| Height: | Above average as compared to other peach cultivars. For example, measurement of a typical grafted tree on 'Lovell' seedling rootstock (unpatented) at four years after planting shows an average height of 3.4 meters when grown in Cream Ridge, New Jersey. |
| Width: | Average as compared to other peach cultivars. For example, measurement of a typical grafted tree on 'Lovell' seedling rootstock (unpatented) at five years after planting shows an average width of 4.6 meters when grown in Cream Ridge, New Jersey. |
| Caliper: | Four year old tree is 32 cm in circumference measured at 20 cm from the ground. |

Trunk and branches:

| | |
|---|---|
| Trunk bark texture: | Fairly smooth with prominent lenticels becoming rough at the tree ages. |
| Trunk bark color: | Under color is greyed-white (RHS 156c). |
| Primary branches: | Branches that are approximately 15 cm in circumference are greyed-orange (RHS 177a) in color, overlaid with greyed-white (RHS 156a). |
| Lenticels: | Moderate density, approximately 2.5 per square cm; elliptical shape; typical examples of which measured 6 mm in length and 2.1 mm in width; greyed-orange (RHS 164a) in color. |

-continued

| | |
|---|---|
| Branch pubescence: | None. |
| New growth bark: | Color between greyed-purple (RHS 183a) and greyed-orange (RHS 166a) in sun; color yellow-green (between RHS 152a and RHS 152b) in shade. |
| Internodes: | Length averaging 28.8 mm on a one-year shoot. |

Leaves:

| | |
|---|---|
| Texture: | Glabrous. |
| Sheen: | Young leaves semi-glossy with a flat finish on the underside. |
| Length: | About 146 mm to 179 mm, averaging about 158 mm including the petiole. |
| Width: | About 31 mm to 38 mm, averaging about 34 mm. |
| Petiole: | Averaging 10.7 mm long and about 1.4 mm in diameter. |
| Margin: | Serrulate. |
| Margin undulation: | Nearly none to slight. |
| Form: | Elliptic. |
| Apex: | Sharply acute, curved downward. |
| Base: | Broadly acute. |
| Venation: | Pinnate. |
| Glands: | |
| Number: | About 2 to 5, averaging about 3.3. |
| Position: | Located primarily on the leaf margin. |
| Size: | Length averaging 1.0 mm and width averaging 0.6 mm. |
| Form: | Reniform. |
| Stipules: | None observed on mature leaves. |
| Leaf Color: | |
| Upper leaf surface: | Yellow-green (between RHS 146a and RHS 148a). |
| Lower leaf surface: | Yellow-green (RHS 147b). |
| Vein: | Greyed-yellow (RHS 160a). |
| Pubescence: | None. |

Flowers:

| | |
|---|---|
| Size: | Large size, typical flower measuring between 14.8 mm to 18.3 mm, averaging about 17.0 mm across. |
| Color: | |
| Dormant bud: | Greyed-green (between RHS 196b and RHS 198c). |
| Pink stage bud: | Red (between RHS 54b and RHS 54c). |
| Open flower: | Young open flowers red (RHS 54c to RHS 54d), and venation becoming red-purple (between RHS 66d) at petal fall. |
| Petals: | Typically five petals per flower; cupped and obovate in shape; averaging 11.9 mm long and 9.8 mm wide. Red (between RHS 54c and RHS 54d) in color. |
| Petal apex: | Rounded. |
| Petal base: | Cuneate. |
| Stamens: | |
| Number: | Variable, typical range 33 and 38, averaging 34.4. |
| Length: | Variable, between 11.5 mm to 14 mm, averaging 12.6 mm. |
| Filament color: | Green-white (RHS 157c). |
| Anther color: | Red (between RHS 42a). |
| Pistil: | |
| Number: | One. |
| Size: | Length between 14.4 and 17.9 mm, averaging about 16.4 mm. |
| Pistil color: | Greyed-yellow (RHS 160a). |
| Ovary: | Dense pubescence and ellipsoid in shape. |
| Sepals: | |
| Number: | Five. |
| Pubescence: | Light. |

-continued

| | |
|---|---|
| Color: | Yellow-green (RHS 146c) with a greyed-red (RHS 182a) over color. |
| Shape: | Triangular, with a rounded apex. |
| Size: | Length averaging 4.8 mm, width averaging 3.9 mm. |
| Nectar cup color: | Greyed-orange (RHS 167a). |
| Pollen: | Abundant; yellow-orange (RHS 16a) in color. |
| Fragrance: | Very slight. |
| Bloom season. | Onset of bloom in 2005 on April 15; full bloom on April 18. |

Fruit:

| | |
|---|---|
| Size: | Large, averaging about 6.8 cm long, 6.7 cm wide parallel to the suture and 6.6 cm wide perpendicular to the suture. |
| Typical weight: | 162 g. |
| Form: | |
| Longitudinal section: | Round. |
| Transverse section: | Round. |
| Suture: | Very shallow, extending form the base to apex. |
| Ventral surface: | Nearly smooth. |
| Base: | Round. |
| Apex: | Round. |
| Stem: | Average length of 7.1 mm and an average diameter of 5.2 mm. |
| Skin: | |
| Thickness: | Average. |
| Surface: | Regular with short pubescence. |
| Tenacity: | Average. |
| Astringency: | None. |
| Tendency to crack: | Very low. |
| Color: | Mottled red (RHS 46a) over an orange-red (RHS 34b) blush; ground color orange-red (between RHS 32d). |
| Fruit Properties: | |
| Flesh color: | Yellow-orange (RHS 15c). |
| Flesh adhesion: | Clingstone. |
| Juice: | Moderate. |
| Texture: | Firm, but melting. |
| Fibers: | Not noticeable. |
| Ripens: | Between June 27 and July 15 at Cream Ridge, New Jersey. |
| Flavor: | Above average for season, moderately acidic. |
| Soluble solids: | 9.7%. |
| Aroma: | Very slight. |
| Eating quality: | Good. |
| Keeping quality: | Average. Has held its flavor and firmness for at least 7 days in cold storage at 1° C. to 4° C. |

-continued

| | |
|---|---|
| Shipping quality: | Very good. Fruit are generally very firm at harvest. No bruising or scaring disorders have been observed. |
| Usage: | Desert. |
| Market: | Local and long distance. |
| Productivity: | Very good. Trees have produced a crop in 6 out of 8 years and a full crop in 6 out of 8 years at Cream Ridge, New Jersey. |

Stone:

| | |
|---|---|
| Type: | Clingstone. |
| Form: | Ovate to obovate. |
| Base: | Medium. |
| Apex: | Medium. |
| Surface: | Pit grooves. |
| Ventral suture: | Medium. |
| Dorsal ridge: | Medium, narrow, and fine lines. |
| External color: | Orange-white (between RHS 159b and RHS 159c), with greyed-orange (between RHS 165b and RHS 165c) grooves. |
| Internal color when cracked: | Orange-white (between RHS 159a and RHS 159b). |
| Cavity surface color: | Greyed-orange (between RHS 165c and RHS 165d). |
| Average stone dry weight: | 4.8 g. |
| Average stone wall thickness: | Varies between 5.1 and 8.8 mm. |
| Size: | Averages about 36 mm long, 26 mm wide parallel to the dorsal ridge, and 20 mm wide perpendicular to the dorsal ridge. |
| Tendency to split: | Very low for ripening season. |
| Kernel: | |
| Form: | Irregular. |
| Skin color: | Greyed-orange (between RHS 165a to RHS 165b). |
| Vein color: | Greyed-orange (between RHS 165a to RHS 165b). |
| Viability: | No. |
| Size: | Highly variable; forms only rudimentary seed. |
| Amygdalin | Present |

Plant/fruit disease and pest resistance/susceptibility: No atypical resistances/susceptibilities have been noted under normal cultural practices.

We claim:

1. A new and distinct variety of peach tree, substantially as herein shown and described.

* * * * *